(12) United States Patent
Petros

(10) Patent No.: US 9,125,949 B2
(45) Date of Patent: Sep. 8, 2015

(54) DIRECT UTILIZATION OF PLASMA PROTEINS FOR THE IN VIVO ASSEMBLY OF PROTEIN-DRUG/IMAGING AGENT CONJUGATES, NANOCARRIERS AND COATINGS FOR BIOMATERIALS

(75) Inventor: Robby A. Petros, Denton, TX (US)

(73) Assignee: University of North Texas, Denton, TX (US)

( * ) Notice: Subject to any disclaimer, the term of this patent is extended or adjusted under 35 U.S.C. 154(b) by 812 days.

(21) Appl. No.: 12/649,941

(22) Filed: Dec. 30, 2009

(65) Prior Publication Data

US 2010/0168024 A1    Jul. 1, 2010

Related U.S. Application Data

(60) Provisional application No. 61/141,536, filed on Dec. 30, 2008.

(51) Int. Cl.
*A61K 39/00* (2006.01)
*A61K 47/48* (2006.01)

(52) U.S. Cl.
CPC .................. *A61K 47/48246* (2013.01)

(58) Field of Classification Search
None
See application file for complete search history.

(56) References Cited

U.S. PATENT DOCUMENTS

2005/0287153 A1* 12/2005 Dennis ........................ 424/178.1
2006/0058236 A1*  3/2006 Hutchins et al. ................ 514/12
2006/0147380 A1*  7/2006 Lanza et al. ................... 424/9.36
2006/0205037 A1*  9/2006 Sadeghi et al. .............. 435/69.7
2008/0095857 A1*  4/2008 Balthasar et al. ............. 424/499
2009/0191225 A1*  7/2009 Chang et al. ................ 424/181.1

OTHER PUBLICATIONS

Rolland, Maynor, Euliss, Exner, Denison, and De Simone. Direct fabrication and harvesting of monodisperse, shape-specific nanobiomaterials. Journal of the American Chemical Society, 2005. vol. 127, pp. 10096-10100.*
Reis et al., Nanomedicine. Mar. 2006;2(1):8-21.*
Ogawara et al., J Control Release. Dec. 10, 2004;100(3):451-5.*
Aina, O.H., et al., "From combinatorial chemistry to cancer-targeting peptides", Molecular Pharmaceutics (2007), 4:5, 631-651.
Castner, D.G., et al., "Biomedical surface science: Foundations to frontiers", Surface Science (2002) 500:1-3, 28-60.
Kratz, F., et al., "Probing the cysteine-34 position of endogenous serum albumin with thiol-binding doxorubicin derivatives. Improved efficacy of an acid-sensitive doxorubicin derivative with specific albumin-binding properties compared to that of the parent compound", J. Med. Chem. (2002) 45:5523-5533.
Kratz, F., et al., "Prodrug strategies in anticancer chemotherapy", Chem Med Chem (2008) 3:1, 20-53.
Liu, L. Y. et al., "Reduced foreign body reaction to implanted biomaterials by surface treatment with oriented osteopontin", Journal of Biomaterials Science-Polymer Edition (2008) 19:6, 821-835.
Moghimi, S. M., et al., "Long-circulating and target-specific nanoparticles: theory to practice", Pharmacol Rev (2001) 53:2, 283-318.

* cited by examiner

*Primary Examiner* — Michael Szperka
(74) *Attorney, Agent, or Firm* — Chainey P. Singleton; Edwin S. Flores; Chalker Flores, LLP

(57) ABSTRACT

The present invention includes compositions and methods for making and using a drug conjugated to a peptide or protein that binds specifically to a ligand in vivo, wherein the conjugate binds to its ligand in vivo and increases the half-life of the drug.

14 Claims, 1 Drawing Sheet

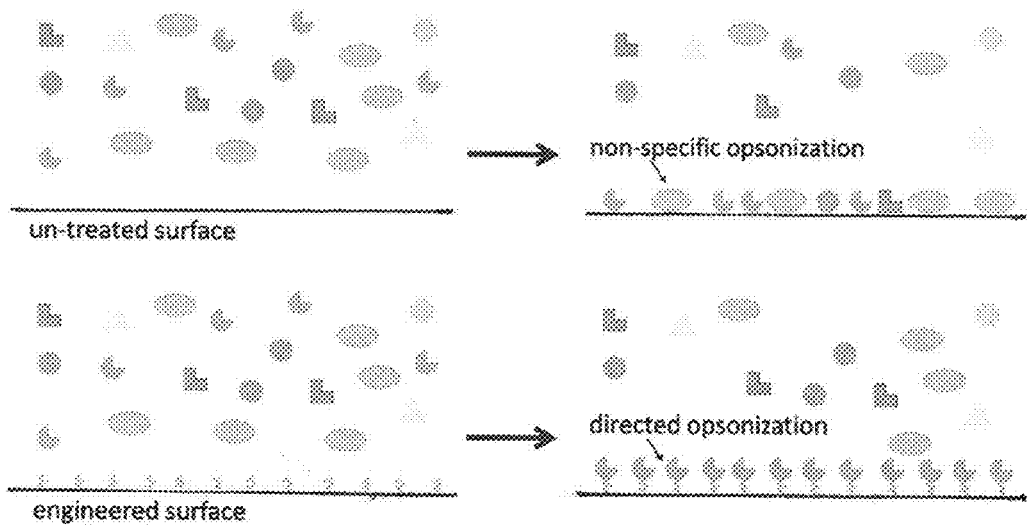

DIRECT UTILIZATION OF PLASMA PROTEINS FOR THE IN VIVO ASSEMBLY OF PROTEIN-DRUG/IMAGING AGENT CONJUGATES, NANOCARRIERS AND COATINGS FOR BIOMATERIALS

TECHNICAL FIELD OF THE INVENTION

The present invention relates in general to the field of in vivo assembly of conjugates, and more particularly, to compositions and methods for the targeted delivery of active agents in in vivo.

STATEMENT OF FEDERALLY FUNDED RESEARCH

None.

CROSS-REFERENCE TO RELATED APPLICATIONS

This application claims benefit of U.S. Provisional Application Ser. No. 61/141,536 filed on Dec. 30, 2008, which is incorporated herein by reference in its entirety.

INCORPORATION-BY-REFERENCE OF MATERIALS FILED ON COMPACT DISC

None.

BACKGROUND OF THE INVENTION

Without limiting the scope of the invention, its background is described in connection with the delivery of active agents in vivo.

It is well known that low-molecular weight pharmaceutics are rapidly cleared from circulation following intravenous injection. This restricts the amount of time a therapeutically relevant dose can be maintained and greatly limits the effectiveness of many of these compounds. A great deal of research has been conducted in an effort to prolong plasma residence times via conjugation to macromolecular constructs that display extended circulation profiles, such as polymers or proteins. However, these methods require the conjugation to be carried out ex vivo.

One such method is taught in U.S. Pat. No. 7,344,698, issued to Lanza, et al., for Integrin targeted imaging agents. Briefly, this patent teaches emulsions of nanoparticles formed from high boiling liquid perfluorochemical substances, wherein the particles are coated with a lipid/surfactant coating are made specific to regions of activated endothelial cells by coupling said nanoparticles to a ligand specific for $\alpha_v\beta_3$ integrin, other than an antibody. The nanoparticles may further include biologically active agents, radionuclides, or other imaging agents.

Yet another example is U.S. Pat. No. 6,818,630, issued to Duncan, et al., for biologically active materials, particularly materials that comprise a biodegradeable polymer, linked to a biologically active agent. The patent is said to teach materials known as polymer-drug conjugates that typically contain a therapeutic agent, for instance a bioactive cytotoxic drug linked to a polymer backbone (the linkage is typically a convalent linkage). In some embodiments the disclosure concerns other polymer conjugates including those where the biologically active agent is an imaging agent, such as a tyrosinamide, a diagnostic agent, or a targeting agent, such as biotin.

Yet another example is U.S. Pat. No. 5,965,131, issued to Griffiths, et al., for the delivery of diagnostic and therapeutic agents to a target site. Briefly, this patent teaches improved in vivo pretargeting methods for delivering diagnostic or therapeutic agents to a target site in a mammal uses a clearing agent that binds to the target-binding site of the targeting species, whereby non-bound primary targeting species is cleared from circulation but the clearing agent does not remove the bound primary targeting species. Anti-idiotype antibodies and antibody fragments are preferred clearing agents. Fast clearance is achieved by glycosylating the clearing agent with sugar residues that bind to the hepatic asialoglycoprotein receptor.

SUMMARY OF THE INVENTION

In one embodiment, the present invention includes compositions and methods for targeted drug delivery comprising: identifying a patient in need of drug therapy; attaching a drug to a molecular recognition element to form a drug-molecular recognition element conjugate that binds specifically to a target in vivo, and treating the patient with the conjugate, wherein the conjugate binds its ligand in vivo and increases the half-life of the drug. In one aspect, the ligand comprises a serum protein, a cell surface, a cancer, or a tissue. In another aspect, the drug and the molecular recognition element are conjugated by a biodegradable linker. In another aspect, the drug and the molecular recognition element are conjugated by a cleavable linker. In another aspect, the drug and the molecular recognition element are conjugated by a stimuli-responsive cleavable linker. In another aspect, the molecular recognition element binds to its ligand in vivo with an affinity greater than 100 nM. In another aspect, the molecular recognition element is multimeric and generates plasma protein-based nanoparticles in vivo. In another aspect, the molecular recognition element directs assembly of a protective protein coat to the surface of nanoparticles in vivo. In another aspect, the molecular recognition element binds a biomaterial surface and directs protein opsonization to the biomaterials surface.

In another embodiment, the present invention includes a composition comprising a drug conjugated to a molecular recognition element that binds specifically to a ligand in vivo, wherein the conjugate binds to its ligand in vivo and increases the half-life of the drug. In another embodiment, the present invention includes a composition comprising a drug conjugated to a peptide or protein that binds specifically to a ligand in vivo, wherein the conjugate binds to its ligand in vivo and increases the half-life of the drug. In one aspect, the ligand comprises a serum protein, a cell surface, a cancer, or a tissue. In another aspect, the drug and the molecular recognition element are conjugated by a biodegradable linker. In another aspect, the drug and the molecular recognition element are conjugated by a cleavable linker. In another aspect, the drug and the molecular recognition element are conjugated by a stimuli-responsive cleavable linker. In another aspect, the molecular recognition element binds to its ligand in vivo with an affinity greater than 100 nM. In another aspect, the molecular recognition element is multimeric and generates plasma protein-based nanoparticles in vivo. In another aspect, the molecular recognition element directs assembly of a protective protein coat to the surface of nanoparticles in vivo. In another aspect, the molecular recognition element binds a biomaterial surface and directs protein opsonization to the biomaterials surface.

The present invention also include a composition and a method for targeted drug delivery comprising: identifying a patient in need of drug therapy; attaching a drug to a peptide or protein to form a drug-ligand binding peptide or protein conjugate that binds specifically to a ligand in vivo; and treating the patient with the conjugate, wherein the conjugate binds its ligand in vivo and increases the half-life of the drug. In yet another embodiment, the present invention includes a composition and a method of making the composition for targeting a ligand for delivery of a drug in vivo comprising identifying a ligand, isolating a ligand-specific molecular recognition element specific for the ligand, wherein the molecular recognition element is capable of binding to the ligand in vivo, and attaching a drug to the molecular recognition element. In one aspect, the ligand comprises a serum protein, a cell surface, a cancer, or a tissue. In another aspect, the drug and the molecular recognition element are conjugated by a biodegradable linker. In another aspect, the drug and the molecular recognition element are conjugated by a cleavable linker. In another aspect, the drug and the molecular recognition element are conjugated by a stimuli-responsive cleavable linker. In another aspect, the molecular recognition element binds to its ligand in vivo with an affinity greater than 100 nM. In another aspect, the molecular recognition element is multimeric and generates plasma protein-based nanoparticles in vivo. In another aspect, the molecular recognition element directs assembly of a protective protein coat to the surface of nanoparticles in vivo. In another aspect, the molecular recognition element binds a biomaterial surface and directs protein opsonization to the biomaterials surface.

BRIEF DESCRIPTION OF THE DRAWINGS

For a more complete understanding of the features and advantages of the present invention, reference is now made to the detailed description of the invention along with the accompanying figures and in which:

FIG. 1 shows the direct opsonization method of the present invention in which the opsonizing molecules are pre-attached to the surface using direct conjugation rather than random binding.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention can be used to target a wide variety of proteins, carbohydrates, lipids and combinations thereof for both the delivery and targeting of the molecules.

As used herein, the term "antibody" refers to a protein produced by a mammalian immune system that binds tightly and specifically to particular molecules.

As used herein, the term "antigen" refers to a ligand that is bound specifically by an antibody.

As used herein, the term "biodegradable" refers to degradation in a biological system, for example, enzymatic degradation or chemical degradation. For example, a biodegradable linker is a chemical moiety that is degradable under physiologic conditions and that upon degradation releases previously linked into individual molecular entities.

As used herein, the terms "drug," "therapeutic," or "active agent" refer to any molecule, molecular complex or substance administered to an organism for diagnostic or therapeutic purposes, including the treatment of a disease or infection, medical imaging, monitoring, contraceptive, cosmetic, nutraceutical, pharmaceutical and prophylactic applications. The term "drug" includes any such molecule, molecular complex or substance that is chemically modified and/or operatively attached to a biologic or biocompatible structure. The term "prodrug" refers to a drug, drug precursor or modified drug that is not fully active or available until converted in vivo to its therapeutically active or available form. The term "prodrug complex" refers to a prodrug comprising at least two noncovalently bound molecules and includes, without limitation, a drug specifically bound to a synthetic receptor. The term "multi-prodrug complex," also described herein as a "multi-prodrug reservoir," refers to a prodrug complex comprising at least two drug molecules specifically bound to at least two synthetic receptors.

As used herein, the terms "specifically bind," "specifically bound" and "specific binding" refer to saturable, noncovalent interaction between a ligand and a receptor that can be competitively inhibited by structural analogs of the ligand.

As used herein, the term "ligand" refers to any serum protein, host cell, cell surface antigen, cell surface receptor, or host organ that may be used to be bound to the molecular recognition element in vivo. Other non-limiting examples of ligands include growth factors, cytokines, prosthetic groups, coenzymes, cofactors, regulatory factors, antigens, receptors, haptens, vitamins, nucleic acids and natural or synthetic heteropolymers comprising amino acids, nucleotides, carbohydrates or non-biologic monomers, including analogs and derivatives thereof, and conjugates or complexes formed by attaching or binding any of these molecules to a second molecule. Generally, the ligands for the present invention are serum proteins.

As used herein, the term "receptor" refers to a specific binding partner of a ligand and includes, without limitation, membrane receptors, soluble receptors, cloned receptors, recombinant receptors, hormone receptors, drug receptors, transmitter receptors, autacoid receptors, cytokine receptors, antibodies, antibody fragments, engineered antibodies, antibody mimics, molecular recognition units, adhesion molecules, agglutinins, integrins, selectins, nucleic acids and synthetic heteropolymers comprising amino acids, nucleotides, carbohydrates or non-biologic monomers, including analogs and derivatives thereof, and conjugates or complexes formed by attaching or binding any of these molecules to a second molecule.

As used herein, the term "drug-ligand binding peptide conjugate" or "drug-ligand binding protein conjugate" refers to a molecule that includes two domains, one domain that binds specifically to a ligand in vivo, and a second domain that includes a drug. For example, the present invention may include a drug-ligand binding peptide or protein conjugate that includes an antibody or fragment thereof (e.g., a humanized antibody fragment) that binds specifically to a serum protein (e.g., Complement cascade proteins, albumin, LDL, HDL, VLDL) and that forms a conjugate in vivo that then helps deliver the drug to a target within the body. In one example, the drug-ligand binding peptide or protein conjugate modifies the half-life of the drug (for example increases the half life) and can also increase the relative concentration of the drug at the target site.

As used herein, the term "molecular recognition element" refers to molecules capable of specifically (i.e., non-randomly) binding to, hybridizing to, or otherwise interacting with a desired ligand molecule. Examples of molecular recognition elements include, but are not limited to, polypeptides (e.g., antigen binding proteins, receptor ligands, signal peptides, hydrophobic membrane spanning domains), antibodies (and portions thereof), nucleic acid molecules (e.g., RNA and DNA, including ligand-binding RNA molecules), organic molecules (e.g., biotin, carbohydrates, glycoproteins), and inorganic molecules (e.g., vitamins). A given drug may be bound to one or more molecular recognition elements.

As used herein, the term "target" refers to cells, organs or the organism in need to treatment with a drug or active agent. In certain cases, the target will be diseases cells, disease causing cells, autoimmune, microorganism, bacteria, virus, fungus, plant, protozoa, or pathogen or portion of an organism, cell, microorganism, bacteria, virus, fungus, plant, prion, protozoa or pathogen.

Other methods for screening ligands for protein binding can be envisioned. Methods which are "low through-put" are less desirable than high through-put ones such as a one-bead-one-compound (OBOC) peptide library. Other methods are known for generating combinatorial peptide libraries.

The present invention provides compositions and methods for enhancing immune responses will likely be possible using methods outlined here. Many cancer types avoid immune recognition through tolerance mechanisms. This tolerance could be overcome by selectively tagging proteins on the surface of cancer cells with stimulatory signals for the immune system, such as tagging with non-specific IgG.

Example 1

Novel Small-Molecule Conjugates Capable of Binding with High Affinity to Plasma Proteins Low-molecular weight pharmaceutics are rapidly cleared from circulation following intravenous injection. Rapid clearing restricts the amount of time a therapeutically relevant dose can be maintained and greatly limits the effectiveness of many of these compounds. A great deal of research has been conducted in an effort to prolong plasma residence times via conjugation to macromolecular constructs that display extended circulation profiles, such as polymers or proteins. Prior art methods almost exclusively require the conjugation to be carried out ex vivo. An in vivo method is more desirable, and this embodiment of the invention encompasses a method for attaching the low molecular weight therapeutics to specific proteins in vivo to extend their plasma half-lives. The conjugate includes a molecular recognition element (e.g., a protein or peptide that specifically binds to a ligand in vivo) specific for a desired plasma protein and a therapeutic. For example, a ligand that binds non-covalently to albumin with high-affinity and selectivity is elucidated by using a one-bead-one-compound (OBOC) peptide library used to find molecular recognition elements (also referred to herein as targeting ligands) for, e.g., cancer cells. A high-affinity ligand is linked to a therapeutic molecule through either a degradable or non-degradable linker. When administered by intravenous injection, this conjugate should selectively bind to albumin in circulation, which reduces the rate of clearance of the therapeutic. Two aspects of the conjugate are important: 1) choice of ligand protein—a wide variety of plasma proteins can be targeted including: albumin, transferrin, as well as proteins expressed on the surface of red blood cells, etc., with the identity of the ligand protein altering the biodistribution of the therapeutic and engendering the ability to target specific cells or tissues, 2) the release of the therapeutic can be facilitated by either tailoring the affinity of the molecular recognition element or targeting ligand for it's ligand to achieve the desired release rate profile or by incorporating a stimuli-responsive linker between the molecular recognition element and the drug, therapeutic or active agent.

Example 2

Nanoparticles Assembled In Vivo

Conjugates described in example 1 in which the targeting ligand is made multimeric are used to generate plasma protein-based nanoparticles in vivo. Therapeutics contained in these nanoparticles can display significantly different biodistribution profiles compared to free therapeutic or even conjugates from example 1. Release of therapeutic is achieved as outlined in example 1.

Example 3

Directed Assembly of a Protective Protein Coat to the Surface of Nanoparticles In Vivo Plasma protein targeting ligands such as those described in example 1 are conjugated to the surface of nanoparticles to facilitate the binding of target proteins to the surface of the particle upon intravenous injection. The proteins bound as a result of binding camouflage the particle and reduce particle recognition by cells of the immune system, such as macrophages, thereby extending the circulation time of the nanoparticle.

Example 4

Directed Protein Opsonization to Biomaterials Surfaces

Custom-tailored materials find widespread use in drug delivery, tissue engineering, bioanalytical chemistry, and implantable medical devices. Despite their widespread use, a detailed understanding of how these materials interact with living systems is still lacking. When a material is introduced to the body, a complex series of events ensue beginning with protein adsorption to the surface of the material (opsonization), which leads either to local inflammation or to sequestration of the material by cells of the immune system. In the case of an implanted material, the foreign body response (FBR) universally occurs. This response begins with opsonization, which leads to inflammation and ultimately to encapsulation of the material in a dense fibrous coat. Macrophages, a sub-set of leukocytes, play an important role in FBR. When they encounter an implanted material, they remain at the wound site indefinitely eventually fusing together to form foreign body giant cells (FBGC) at the material/tissue interface. These cells, observed exclusively during FBR, release toxic and inflammatory compounds at the wound site.

Opsonization plays a central role in the activation of the immune system. It begins immediately after a material comes in contact with plasma. The exact nature of the types and quantities of proteins, and their conformations, dictate the body's reaction to the material. It is therefore paramount that this process be harnessed and used to orchestrate desired outcomes based on application-specific requirements. The mechanisms involved are not well understood; however, the major opsonins are known. Immunoglobulin and complement proteins are the predominant contributors to the recognition of foreign materials by macrophages. Immunoglobulin adsorbed to the surface binds to macrophages through an Fc receptor on the macrophage. This attachment results in adherence to the material and possibly to internalization depending on the size of the material relative to that of the cell. Adsorption of complement protein C3 can induce conformational changes in the protein's structure that activate it toward cleavage to C3b. Macrophages express a receptor to C3b (CR1), which again facilitates attachment to the material.

FIG. 1 shows the direct opsonization method of the present invention in which the opsonizing molecules are pre-attached to the surface using direct conjugation rather than random binding.

This example of the invention describes the elucidation of peptide-based ligands capable of high-affinity binding to specific plasma proteins like those described in example 1. These ligands, when immobilized on the surfaces of biomaterials, direct protein adsorption in vivo. For example, a high-affinity peptide ligand for albumin bound to the surface of a material adsorbs albumin upon exposure to plasma (albumin makes up ~60% of blood protein). Similarly, a material coated with a high-affinity peptide ligand for transferrin will bind that protein when exposed to plasma. Using this method controls which proteins adsorb to the surface of biomaterials, and in what proportions.

Methods used extensively in the search for cancer targeting ligands are employed to identify short peptide sequences capable of binding to various plasma proteins. Using a one-bead-one-compound (OBOC) library, $1\times10^4$-$1\times10^8$ individual peptide sequences are generated via traditional solid-phase peptide synthesis (TantaGel S NH$_2$ resin, 130 μm). A 4-hydroxymethylbenzoic acid resin linker is used to facilitate sequencing via MALDI-TOF mass spec analysis. Beads are screened for binding to the desired fluorescently-labeled protein. Positive hits will be identified via fluorescence microscopy, removed from solution using a micro-pipette, and analyzed by mass spec. A batch of beads with only this peptide on the surface is synthesized. These beads are incubated with plasma and the identities of bound proteins determined via standard methods.

This invention makes possible the in vivo recruitment of proteins to the material surface that can be used to dictate the body's response to the material. Vascular endothelial growth factor (VEGF) can be recruited to promote wound healing and ligands capable of binding to inhibitory receptors expressed by macrophages will be used to decrease inflammation near the biomaterial surface. Cell-type specific ligands will be used to promote selective colonization of the biomaterial surface.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Aina, O. H.; Liu, R. W.; Sutcliffe, J. L.; Marik, J.; Pan, C. X.; Lam, K. S., From combinatorial chemistry to cancer-targeting peptides. Molecular Pharmaceutics 2007, 4, (5), 631-651.

Castner, D. G.; Ratner, B. D., Biomedical surface science: Foundations to frontiers. Surface Science 2002, 500, (1-3), 28-60.

Kratz, F.; Warnecke, A.; Scheuermann, K.; Stockmar, C.; Schwab, J.; Lazar, P.; Druckes, P.; Esser, N.; Drecs, J.; Rognan, D.; Bissantz, C.; Hinderling, C.; Folkers, G.; Fichtner, I.; Unger, C. "Probing the cysteine-34 position of endogenous serum albumin with thiol-binding doxorubicin derivatives. Improved efficacy of an acid-sensitive doxorubicin derivative with specific albumin-binding properties compared to that of the parent compound" J. Med. Chem., 2002, 45, 5523-5533.

Kratz, F.; Muller, I. A.; Ryppa, C.; Warnecke, A., Prodrug strategies in anticancer chemotherapy. Chem Med Chem 2008, 3, (1), 20-53.

Liu, L. Y.; Chen, G.; Chao, T.; Ratner, B. D.; Sage, E. H.; Jiang, S. Y., Reduced foreign body reaction to implanted biomaterials by surface treatment with oriented osteopontin. Journal of Biomaterials Science-Polymer Edition 2008, 19, (6), 821-835.

Moghimi, S. M.; Hunter, A. C.; Murray, J. C., Long-circulating and target-specific nanoparticles: theory to practice. Pharmacol Rev 2001, 53, (2), 283-318.

What is claimed is:

1. A composition comprising:
   a drug disposed in a nanoparticle;
   a degradable linker conjugated to the surface of the nanoparticle; and
   a blood serum protein binding peptide connected to the degradable linker, wherein the blood serum protein binding peptide binds specifically to one or more blood serum proteins in vivo to form a protective protein coat about the drug in vivo to mask the nanoparticle.

2. The composition of claim 1, wherein the drug nanoparticle and the blood serum protein binding peptide are conjugated by a biodegradable linker.

3. The composition of claim 1, wherein the drug nanoparticle and the blood serum protein binding peptide are conjugated by a cleavable linker.

4. The composition of claim 1, wherein the drug nanoparticle and the blood serum protein binding peptide are conjugated by a stimuli-responsive cleavable linker.

5. The composition of claim 1, wherein the blood serum protein binding peptide binds to the one or more blood serum proteins with an affinity greater than 100 nM.

6. The composition of claim 1, wherein the blood serum protein binding peptide directs protein opsonization to the drug.

7. A masked drug loaded nanoparticle comprising
   a drug loaded nanoparticle conjugated by a degradable linker to a blood serum protein binding peptide that binds specifically to one or more blood serum proteins in vivo to direct a blood serum protein opsonization to the drug loaded nanoparticle.

8. The masked drug loaded nanoparticle of claim 7, wherein the drug nanoparticle and the peptide are conjugated by a cleavable linker.

9. The masked drug loaded nanoparticle of claim 7, wherein the blood serum protein binding peptide binds to the one or more blood serum proteins with an affinity greater than 100 nM.

10. The masked drug loaded nanoparticle of claim 7, wherein the blood serum protein binding peptide directs assembly of a protective blood serum protein coat to the drug loaded nanoparticle in vivo.

11. A method of making a composition for targeting a ligand for masking delivery of a drug loaded nanoparticle in vivo comprising the steps of:
    identifying a blood serum ligand;
    isolating a ligand-specific molecular recognition element that binds specifically to the blood serum ligand in vivo;
    providing a drug loaded nanoparticle;
    binding the drug loaded nanoparticle to the ligand-specific molecular recognition element using a degradable linker; and
    when injected in to a subject the blood serum ligand binds to the ligand-specific molecular recognition element to undergo blood serum ligand opsonization in vivo and the drug loaded nanoparticle is masked by the blood serum ligand and the drug can be released from the drug loaded nanoparticle.

12. A composition made by the method of claim 11.

13. A masking composition comprising
    a nanoparticle carrier suitable for intravenous delivery;
    a drug disposed in the nanoparticle carrier; and
    a molecular recognition element conjugated by a degradable linker to the nanoparticle, wherein the molecular recognition element binds specifically to one or more blood serum proteins in vivo to form a protective blood serum protein coat that masks the nanoparticle in the blood, while allowing release of the drug from the nanoparticle.

14. A masking drug nanoparticle composition comprising:
    a carrier suitable for intravenous delivery;
    one or more molecular recognition elements disposed in the carrier, wherein the one or more molecular recognition elements binds specifically to one or more blood serum proteins in vivo; and
    a drug nanoparticle conjugated to the one or more molecular recognition elements by a degradable linker, wherein the one or more blood serum proteins bind to the molecular recognition element to form a protective blood serum protein coat that masks the drug nanoparticle in vivo, wherein the one or more molecular recognition elements are multimeric and generate one or more plasma protein-based nanoparticles in vivo.

* * * * *